United States Patent [19]

Yamashita et al.

[11] Patent Number: 4,973,695
[45] Date of Patent: Nov. 27, 1990

[54] PROCESS FOR PREPARING PYRIDINE-2,3-DICARBOXYLIC ACID COMPOUNDS

[75] Inventors: Takaharu Yamashita; Mitsuhiro Kodama, both of Wakayama; Shouzo Shimada, Osaka, all of Japan

[73] Assignee: Sugai Chemical Ind. Co., Ltd., Wakayama, Japan

[21] Appl. No.: 308,524

[22] Filed: Feb. 10, 1989

Related U.S. Application Data

[63] Continuation-in-part of Ser. No. 139,641, Dec. 30, 1987, abandoned.

[30] Foreign Application Priority Data

Jan. 6, 1987 [JP] Japan .................................. 62-915
Nov. 16, 1987 [JP] Japan .............................. 62-290389

[51] Int. Cl.$^5$ .................. C07D 213/08; C07D 213/14; C07D 213/80
[52] U.S. Cl. ..................................... 546/250; 546/319
[58] Field of Search ........................ 546/319, 321, 250

[56] References Cited

U.S. PATENT DOCUMENTS 4,460,776 7/1984 Wepplo ............................... 546/250
4,723,011 2/1988 Doehner .............................. 546/250

FOREIGN PATENT DOCUMENTS 0161221 5/1986 European Pat. Off. ............ 546/250
0220518 5/1987 European Pat. Off. ............ 546/250

OTHER PUBLICATIONS

Frank et al., Journal of The American Chemical Society, vol. 71, No. 8, pp. 2629-2635, Aug. 1949.
Journal of Organic Chemistry Soc., vol. 21, p. 800, 1956.

*Primary Examiner*—Alan L. Rotman
*Attorney, Agent, or Firm*—Finnegan, Henderson, Farabow, Garrett & Dunner

[57] ABSTRACT

A process for preparing pyridine-2,3-dicarboxylic acid compounds of the following formula:

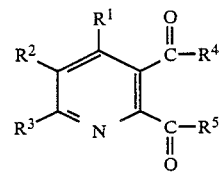

wherein $R^1$ and $R^3$ are, identical or different, each a hydrogen atom or a lower alkyl group, $R^2$ is a hydrogen atom, a lower alkyl group, or a phenyl-(lower)alkyl group which may have halogen atom or lower alkyl group on its phenyl ring, and $R^4$ and $R^5$ are, identical or different, each a lower alkoxy group.

The compounds are useful as an intermediate for preparing agricultural chemicals and pharmaceuticals.

9 Claims, No Drawings

PROCESS FOR PREPARING PYRIDINE-2,3-DICARBOXYLIC ACID COMPOUNDS

CROSS-REFERENCE TO RELATED APPLICATION

This application is a continuation-in-part of application Ser. No. 139,641, filed Dec. 30, 1987, now abandoned.

BACKGROUND OF THE INVENTION

1. Field of the Invention

This invention relates to a process for preparing pyridine-2,3-dicarboxylic acid compounds. More particularly, it relates to a process for preparing pyridine-2,3-dicarboxylic acid compounds which are useful as an intermediate for manufacturing agricultural chemicals and pharmaceuticals.

2. Description of the Prior Art

The pyridine-2,3-dicarboxylic acid compounds are useful intermediates for 2-(2-imidazolin-2-yl)pyridine-3-carboxylic acid derivatives having weeding action as disclosed, for example, in European Patent Application Publication No.A-0041623.

Heretofore, as the method of preparing pyridine-2,3-dicarboxylic acid compounds known are:

(1) Oxidation with nitric acid of quinolines and quinolinols which are synthesized by Skraup reaction from aniline and glycerine with concentrated sulfuric acid and nitrobenzene. (J. Chem. Soc. page 4433, 1956);

(2) Reacting an α, β-unsaturated hydrazone compound and a maleic acid compound in an inert solvent to obtain 1-(substituted amino)-1,4-dihydropyridine-2,3-dicarboxylic acid derivative. Then, heating the resultant derivative to eliminate the substituted amino group in the 1-position. (Japanese Patent Application Unexamined Publication No.246369/1985);

(3) Treating a 1-(substituted amino)-1,2,3,4-tetrahydropyridine-2,3-dicarboxylic acid derivative with acid and/or by heat to convert into a 1,4-dihydropyridine-2,3-dicarboxylic acid derivative, and then oxidizing it. (Japanese Patent Application Unexamined Publication No.47482/1986); and (4) Oxidizing quinoline with excess hypochlorites in the presence of ruthenium oxide. (Japanese Patent Application Unexamined Publication No.212563/1986)

As the method of synthesizing pyridinemonocarboxylic acid derivatives known is such a method as subjecting ethyl 2-methyl-1,4-dihydronicotinate which is produced by condensation and cyclization of α, β-unsaturated aldehydes such as acrolein and crotonaldehyde with ethyl β-aminocrotonate to oxidation with nitric acid in a mixed acid. (J. Org. Chem. Soc. Vol. 21, page 800, 1956)

However, the above method (1) not only has many reaction processes but also requires drastic oxidation with nitric acid, and involves possible hazards. Also, the pyridine-2,3-dicarboxylic acids, which are apt to cause decarboxylation, result in low yields by the oxidation with nitric acid, and, in addition, produce a large quantity of acidic waste liquid. Thus, the method (1) is not suited to the industrial manufacture of pyridine-2,3-dicarboxylic acids.

The methods (2) and (3) mentioned above have many reaction processes leading to decreased total yields, and require the use of expensive starting materials. Particularly, they require elimination process of the substituted amino group in the intermediate. This decreases the yield and is a problem on resource saving. Therefore, it is difficult to manufacture pyridine-2,3-dicarboxylic acid derivatives industrially by the method (2) or (3).

In the method (4), there are problems that a large excess of the oxidant must be used and that a large quantity of waste liquid is produced requiring expenses for its disposal.

SUMMARY OF THE INVENTION

Accordingly, it is an object of this invention to provide a process for preparing pyridine-2,3-dicarboxylic acid compounds in high yields by a reaction completing in one process from starting materials inexpensive and easily available.

The foregoing object is accomplished by providing a process for preparing pyridine-2,3-dicarboxylic acid compounds shown by the formula (1):

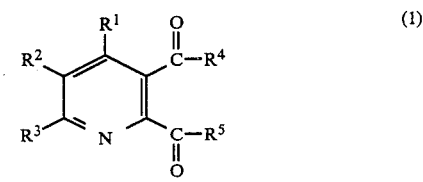

wherein $R^1$ and $R^3$ are, identical or different, each a hydrogen atom or a lower alkyl group, $R^2$ is a hydrogen atom, a lower alkyl group, or a phenyl-(lower)alkyl group which may have halogen atom or lower alkyl group on its phenyl ring, and $R^4$ and $R^5$ are, identical or different, each a lower alkoxy group, which comprises, (1) reacting a compound of the formula (2):

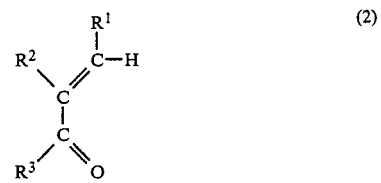

wherein $R^1$, $R^2$, and $R^3$ are same as defined above, a compound of the formula (3):

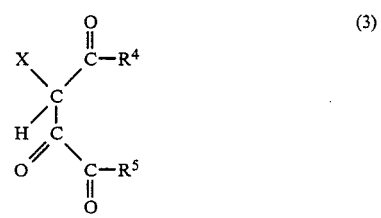

wherein $R^4$ and $R^5$ are same as defined above, and X represents a halogen atom, and ammonia, or (2) reacting a compound of the formula (2):

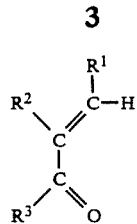

wherein $R^1$, $R^2$, and $R^3$ are same as defined above, and a compound of the formula (4):

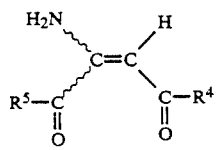

wherein $R^4$ and $R^5$ are same as defined above, in the presence of an acid catalyst.

It is well known by those skilled in the art that the compounds of the above formulae (3) and (4) can exhibit keto-enol or ketimine-enamine tautomerism as exemplified, for example, by the following formula:

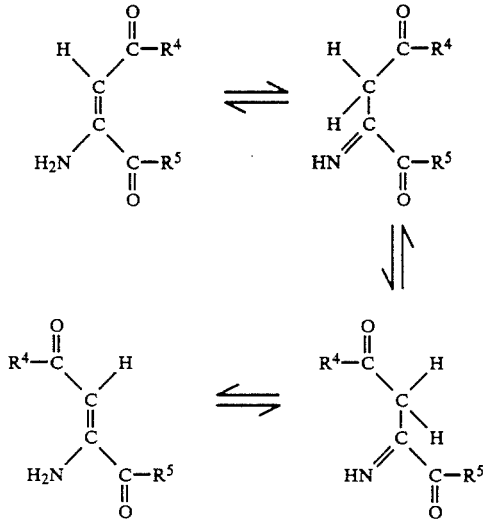

In this specification, such tautomers are represented for convenience' sake by the above structural formulae (3) and (4).

DETAILED DESCRIPTION OF THE INVENTION

Examples of the lower alkyl groups for $R^1$, $R^2$, and $R^3$ in the above formulae include straight or branched alkyl groups having 1 to 8 carbon atoms such as methyl, ethyl, propyl, isopropyl, butyl, isobutyl, tertiary-butyl, pentyl, hexyl, heptyl, octyl and the like.

Examples of the phenyl-(lower)alkyl group for $R^2$ which may have halogen atom or lower alkyl group on its phenyl ring include phenyl-alkyl groups having a straight or branched $C_{1-6}$ alkyl group in the alkyl moiety, and which may have a substituent of halogen atom or straight or branched alkyl group having 1 to 6 carbon atoms on the phenyl ring thereof, for example, benzyl, 2-phenylethyl, 1-phenylethyl, 3-phenylpropyl, 4-phenylbutyl, 5-phenylpentyl, 6-phenylhexyl, 2-methyl-3-phenylpropyl, 4-chlorobenzyl, 3-fluorobenzyl, 2-bromobenzyl, 4-iodobenzyl, 2,4-dichlorobenzyl, 2-(2-fluorophenyl)ethyl, 1-(3-bromophenyl)ethyl, 3-(4-chlorophenyl)propyl, 4-(2-chlorophenyl)butyl, 5-(4-chlorophenyl)pentyl, 6-(4-bromophenyl)hexyl, 4-methylbenzyl, 3-methylbenzyl, 4-ethylbenzyl, 4-isopropylbenzyl, 4-hexylbenzyl, 2-(4-methylphenyl)ethyl, 2-(4propylphenyl)ethyl, 3-(4-methylphenyl)propyl, 3-(3-ethylphenyl)propyl, 4-(4-methylphenyl)butyl, 4-(4-butylphenyl) butyl, 5-(2-methylphenyl)pentyl, 6-(4-hexylphenyl)hexyl and the like.

Examples of the lower alkoxy groups for $R^4$ and $R^5$ include straight or branched alkoxy groups having 1 to 6 carbon atoms such as methoxy, ethoxy, propoxy, isopropoxy, butoxy, isobutoxy, tertiary-butoxy, pentyloxy, hexyloxy and the like.

The halogen atom X may be chlorine atom and bromine atom.

Examples of the compound of the formula (2) include, for example, acrolein, crotonaldehyde, 2-pentenal, 4-methyl-2-pentenal, 2-hexenal, 5-methyl-2-hexenal, 2-heptenal, 2-octenal, 2-nonenal, 2-decenal, 2-undecenal, 2-methyl-2-propenal, 2-ethyl-2-propenal, 2-propyl-2-propenal, 2-isopropyl-2-propenal, 2-butyl-2-propenal, 2-pentyl-2-propenal, 2-hexyl-2-propenal, 2-heptyl-2-propenal, 2-octyl-2-propenal, 2-benzyl-2-propenal, 2-β-phenethyl-2-propenal, 2-(3-phenylpropyl)-2-propenal, 2-(4-chlorobenzyl)-2propenal, 2-(4-bromobenzyl)-2-propenal, 2-(4-methylbenzyl)-2-propenal, 2-(3-methylbenzyl)-2-propenal, 2-(4-ethylbenzyl)-2-propenal, 2-(4-isopropylbenzyl)-2-propenal, 2-methyl-2-butenal, 2-ethyl-2-butenal, 2-benzyl-2-butenal, 2-methyl-2-pentenal, 2-ethyl-2-pentenal, 2-methyl-2-hexenal, 2-ethyl-2-hexenal, 2-methyl-2-heptenal, 2-ethyl-2-heptenal, 2-methyl-2-octenal, 2-ethyl-2-octenal, 2-methyl-2-nonenal, 2-ethyl-2-nonenal, 2-methyl-2-decenal, 2-ethyl-2-decenal, 2-methyl-2-undecenal, 2-ethyl-2-undecenal, 2-hexyl-2-undecenal, 3-buten-2-one, 3-benzyl-3-buten-2-one, 3-(4-chlorobenzyl)-3-buten-2-one, 3-(4-methylbenzyl)-3-buten-2-one, 1-penten-3-one, 3-penten-2-one, 4-hexen-3-one, 3-hepten-2-one, 4-hepten-3-one, 2-hepten-4-one, 3-methyl-3-buten-2-one, 3-ethyl-3-buten-2-one, 2-methyl-1-penten-3-one, 2-ethyl-1-penten-3-one, 4-ethyl-4-hexen-3-one and the like.

Examples of the compound of the formula (3) include, for example, dimethyl α-chlorooxalacetate, diethyl α-chlorooxalacetate, dipropyl α-chlorooxalacetate, diisopropyl α-chlorooxalacetate, dibutyl α-chlorooxalacetate, dipentyl α-chlorooxalacetate, dihexyl α-chlorooxalacetate, methylethyl α-chlorooxalacetate, dimethyl α-bromooxalacetate, diethyl αbromooxalacetate, dipropyl α-bromooxalacetate, diisopropyl α-bromooxalacetate, dibutyl α-bromooxalacetate, dipentyl α-bromooxalacetate, dihexyl α-bromooxalacetate and the like.

Examples of the compound of the formula (4) include, for example, methyl β-amino-β-methoxycarbonylacrylate, ethyl β-amino-β-ethoxycarbonylacrylate, propyl β-amino-β-propoxycarbonylacrylate, isopropyl β-amino-β-isopropoxycarbonylacrylate, butyl β-amino-β-butoxycarbonylacrylate, isobutyl β-amino-β-isobutoxycarbonylacrylate, pentyl β-amino-β-pentyloxycarbonylacrylate, hexyl β-amino-βhexyloxycarbonylacrylate, ethyl β-amino-β-methoxycarbonylacrylate, methyl β-amino-β-ethoxycarbonylacrylate and the like.

The process according to the invention can be represented by the following reaction schemes:

Reaction Scheme 1

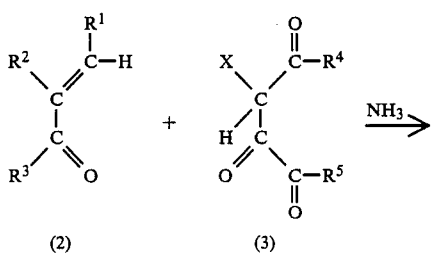

(2)   (3)

Reaction Scheme 2

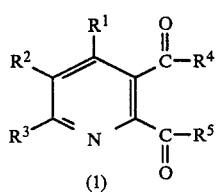

(1)

wherein $R^1$, $R^2$, $R^3$, $R^4$, $R^5$, and X are same defined before.

In the above reaction scheme 1, the reaction of the compound of the formula (2), that of the formula (3), and ammonia is carried out without solvent or in an organic solvent. Any organic solvent, regardless of polarity or protonic property, can be used in the reaction unless it affects the reaction. Such organic solvent may be alcohols such as methanol, ethanol, isopropanol, and butanol; halogenated hydrocarbons such as chloroform, 1,2-dichloroethane, and carbon tetrachloride; aromatic hydrocarbons such as benzene, toluene, xylene, chlorobenzene, o-dichlorobenzene, and nitrobenzene; ethers such as dimethyl ether, diethyl ether, dibutyl ether, tetrahydrofuran, dioxane, ethylene glycol dimethyl ether, ethylene glycol diethyl ether, diethylene glycol dimethyl ether and dibenzyl ether; esters such as methyl acetate and ethyl acetate; aprotic polar solvents, for example, sulfoxides such as dimethy sulfoxide, carboamides such as N,N-dimethylformamide, sulfones such as dimethyl sulfone and sulfolane, and hexamethyl phosphoric triamide, and the like. These organic solvents can be used signly or in a mixture of two or more types. Among these organic solvents, preferable are aprotic organic solvents.

The reaction can be carried out without solvent. The non-solvent method can reduce the cost because of no expences for solvent and solvent recovery and purification.

The reaction temperature of the reaction between the compound of the formula (2), the compound of the formula (3), and ammonia is not limited, but preferably it is in the range of 20° to 200° C., particularly, in the range of 35° to 130° C. For advantageous progress of the reaction, the reaction is preferably carried out under an ammonia gas pressure of 0 to 3 kg/cm$^2$, more preferably 0.3 to 2.5 kg/cm$^2$. The reaction is completed in 30 minutes to 24 hours, generally in 1 to 10 hours. The proportion of the compound of the formula (2) to the compound of the formula (3) is not limited, and can be varied widely. For example, the compound of the formula (2) and the compound of the formula (3) are present in a molar ratio of 0.8:1 to 1.5:1, preferably 1:1 to 1.5:1. Ammonia is usually used in an excess amount to the compounds of the formulae (2) and (3).

To increase the yield of the compound of the formula (1), desired compound in the above reaction, the reaction is carried out in the presence of a secondary or tertiary amine such as dimethylamine, trimethylamine, diethylamine, triethylamine, pyridine, 4-(N,N-dimethylamino)pyridine, morpholine, N-methylmorpholine, 1,5-diazabicyclo-[4.3.0]nonene-5(DBN), 1,4-diazabicyclo[5.4.0]undecene-7(DBU), 1,8-diazabicyclo[2.2.2]octane(DABCO) and the like.

To effectively produce the desired compound, the above reaction is carried out preferably in the presence of an ammonium salt such as ammonium carbonate, ammonium chloride, ammonium sulfate, ammonium nitrate, ammonium phosphate, ammonium acetate and the like.

The secondary and tertiary amines and ammonium salt can be used in adequate quantities, but are used preferably in 0.05 to 1.0 mol per mol of the compound of the formula (3).

In a preferred embodiment of the reaction scheme 1, the compound of the formula (2) and the compound of the formula (3) are reacted under an ammonia gas pressure of 0.3 to 2.5 kg/cm$^2$, without solvent or in an aprotic organic solvent, at temperatures of 70° to 130° C. More preferably, the secondary or tertiary amine and/or the ammonium salt are added to the reaction system in addition.

In the above reaction scheme 2, the compound of the formula (2) and the compound of the formula (4) are reacted in the presence of an acid catalyst without solvent or in an organic solvent.

The acid catalyst used in this reaction may be, for example, inorganic acids such as sulfuric acid, hydrochloric acid, phosphoric acid, hydrobromic acid, and sulfamic acid; organic acids including aliphatic carboxylic acids such as formic acid, acetic acid, propionic acid, oxalic acid, maleic acid, and maleic anhydride, aromatic carboxylic acids such as benzoic acid, sulfonic acids such as benzenesulfonic acid, p-toluenesulfonic acid, and methanesulfonic acid; and acid salts of di- or trialkylamine such as dimethylamine hydrochloride, diethylamine hydrochloride, dimethylamine sulfate, dimethylamine methanesulfonate, trimethylamine hydrochloride, triethylamine hydrochloride, triethylamine benzenesulfonate, morpholine hydrochloride, piperidine hydrochloride, and the like.

The suitable amount of the acid catalyst to be used is 0.02 mol or more per mol of the compound of the formula (4), and when the acid catalyst is a liquid such as formic acid, acetic acid or propionic acid, it is used preferably combined as a solvent.

Any organic solvent can be used in the reaction regardless of the polarity and protonic property, unless it affects the reaction. Such organic solvent is the same as mentioned in the reaction scheme 1.

The reaction temperature of the reaction between the compound of formula (2) and the compound of the formula (4) is not particularly limited, but preferably it is in the range of 20° to 200° C., more preferably in the range of 35° to 150° C. The reaction is completed in 1 to 24 hours, generally in 2 to 10 hours. The reaction is preferably carried out under mild oxidation condition such as bubbling air through the reaction mixture, and the like.

The compounds of the formula (2) and formula (4) can be used in an adequate molar ratio, but preferably the compound of the formula (2) and the compound of the formula (4) are present in a molar ratio of 0.8:1 to 2.0:1, preferably 1:1 to 1.5:1.

The compounds of the formulae (2), (3) and (4) are known or can be synthesized by known methods. For example, the compound of the formula (3) can be prepared by the method described in J. of American Chemical Society, 72, 5221, (1950), and the comound of the formula (4) can be prepared by the method described in Chem. Ber, 98 (9), 2920–5 (1965).

In the compound of the formula (1), carboxylic acid compounds of the formula (1), wherein $R^4$ and/or $R^5$ represent a hydroxy group, can be obtained by subjecting ester compounds of the formula (1), wherein $R^4$ and/or $R^5$ represent an alkoxy group, to hydrolysis. This hydrolysis can be carried out by a conventional method using, for example, an alkali metal hydroxide such as sodium hydroxide and potassium hydroxide. Since the carboxylic acid is readily soluble in water leading to complex separation and purification of the product, the reaction is preferably carried out in a mixed solvent of water and water-insoluble organic solvent such as benzene, toluene, xylene, chlorobenzene etc. in the presence of the basic compound mentioned above, and then the carboxylic acid salt, produced by the hydrolysis, in the water layer is precipitated with a mineral acid such as hydrochloric acid, sulfuric acid, nitric acid, phosphoric acid, etc. This hydrolysis reaction is carried out at room temperature to 150° C., preferably at 40° to 100° C. and completed generally in 1 to 24 hours.

The pyridine-2,3-dicarboxylic acid compound obtained by the process according to the invention is useful as an intermediate for preparing various compounds such as agricultural chemicals and pharmaceuticals. For example, it is a useful intermediate for 2-(2-imidazolin-2-yl)pyridine-3-carboxylic acid derivatives known as a herbicide as disclosed in European Patent Application Publication No.A-0041623.

The process for preparing pyridine-2,3-dicarboxylic acid compounds according to the invention completes the reaction in one step without passing through any intermediate and gives the desired compound in a high yield. It permits the use of inexpensive and readily available starting materials, and the reaction proceeds safely under mild conditions. In addition, the disposal of waste liquid is easy. Thus, the process of the invention can be applied to the industrial scale manufacture of pyridine-2,3-dicarboxylic acid compounds.

EXAMPLES

Hereinafter, this invention will be described in greater detail with reference to Reference Example and Examples, but it should be understood that the invention is not limited to these examples.

REFERENCE EXAMPLE 1

To a mixture of triethylamine hydrochloride 27.5 g (0.20 mol) and 37% formalin 16.3 g (0.201 mol) was added dropwise β-phenylpropionaldehyde 25 g (0.183 mol) at 20° to 35° C. and the mixture was reacted at 110° to 115° C. for 4 hours. After the completion of the reaction, the reaction mixture was cooled to 20° C. and extracted with 100 ml of diethyl ether. The extract was dried over anhydrous sodium sulfate, the solvent was distilled off, and the residue was distilled to give 2-benzyl-2-propenal (bp$_{10}$: 99° to 101° C.) in a yield of 71%.

IR (Neat): 3050 to 2800, 1680 cm$^{-1}$

NMR (CDCl$_3$) ppm: 3.60 (2 H,s), 6.1 (2 H,d), 7.2 (5 H,m).

EXAMPLE 1

In a 1000 ml four neck distillation flask with a reflux condenser were placed chlorobenzene 350 ml and 2-ethyl-2-propenal 21.0 g (0.25 mol) and heated on an oil bath. When the inside temperature was raised to 88° C., a mixture of diethyl α-chlorooxalacetate 44.5 g (0.20 mol) and chlorobenzene 250 ml was added dropwise thereto at 88° to 94° C. for 40 minutes, while the reaction system was being bubbled with dry ammonia gas. After the dropping was completed, the temperature was raised to 115° C. and ammonia gas was bubbled therein further for 4 hours. The reaction mixture was cooled down to room temperature, insoluble matters were filtered off and the filtrate was concentrated. The residue was distilled to give 5-ethyl-2,3-diethoxycarbonylpyridine (bp$_2$: 151° to 152° C.) in a yield of 76.5%.

The above reaction was carried out by use of various solvents. The types of solvent and reaction conditions used, and the yield of the desired compound determined by gas chromatography are shown in Table 1.

TABLE 1

| Solvent | Reaction temperature (°C.) | Reaction time (hr) | Yield (%) |
|---|---|---|---|
| Amyl alcohol | 110 | 4 | 40 |
| Benzene | 76 | 5 | 26.1 |
| Toluene | 105 | 4 | 60.5 |

The 5-ethyl-2,3-diethoxycarbonylpyridine obtained above was hydrolyzed by the method shown below to give 5-ethylpyridine-2,3-dicarboxylic acid.

Toluene 50 ml, 5-ethyl-2,3-diethoxycarbonylpyridine 10.3 g (0.041 mol), and water 29 ml were mixed in a 200 ml four neck distillation flask with a reflux condenser, and 48% aqueous sodium hydroxide solution 21.9 g was added thereto under vigorous stirring in nitrogen atmosphere and refluxed for 3.5 hours. The reaction mixture was allowed to cool to room temperature and stand still to separate into water layer and toluene layer. The water layer was acidified at 45° to 55° C. with 28.3 g of 50% sulfuric acid, and slowly cooled to 20° C. The resultant white crystals were filtered and washed with 10 ml of cold water. Dried under reduced pressure at 50° to 60° C., 5.9 g of 5-ethylpyridine-2,3-dicarboxylic acid was obtained. The melting point of the obtained crystals was 154° to 156° C. (decomposed). The 5-ethylpyridine-2,3-dicarboxylic acid obtained was recrystallized from a mixed solvent of acetone and n-hexane and gave a melting point of 156.5° to 157.5° C. (decomposed).

EXAMPLE 2

Toluene 120 ml was mixed with diethyl α-chlorooxalacetate 9.4 g (0.042 mol) and 2-ethyl-2-propenal 4.2 g (0.05 mol) in a glass autoclave. with an ammonia pressure held to 0.5 kg/cm$^2$, the temperature in the autoclave was raised from 20° C. to 100° C. over a period of about 30 minutes. After further reacting at 100° C. for 4 hours, the contents of the autoclave were allowed to cool to room temperature, and insoluble matters were filtered off. The production of 5-ethyl-2,3-diethoxycarbonylpyridine in a yield of 66.6% was observed by the analysis of the filtrate using gas chromatography.

The above reaction was carried out by use of various solvents. The types of solvent, reaction conditions, and the yield of the desired compound are shown in Table 2.

TABLE 2

| Solvents | Ammonia pressure (kg/cm²) | Reaction temperature (°C.) | Reaction time (hr) | Yield (%) |
|---|---|---|---|---|
| Chloroform | 2.5 | 100 | 13 | 64.0 |
| Benzene | 0.5 | 80 | 8 | 69.5 |
| o-Dichlorobenzene | 0.5 | 110 | 4 | 66.4 |
| Dibenzyl ether | 0.5 | 110 | 4 | 78.3 |
| Diethylene glycol dimethyl ether | 0.5 | 110 | 4 | 78.8 |

EXAMPLE 3

Toluene 120 ml was mixed with diethyl α-chlorooxalacetate 9.4 g (0.042 mol), 2-ethyl-2-propenal 4.2 g (0.05 mol), and triethylamine 0.9 g (0.009 mol) in a glass autoclave. With an ammonia pressure held to 0.5 kg/cm², the temperature in the autoclave was raised from 20° C. to 100° C. over a period of about 30 minutes. After further reaction at 100° C. for 4 hours, the contents of the autoclave were allowed to cool to room temperature, and insoluble matters were filtered off. The production of 5-ethyl-2,3-diethoxycarbonylpyridine in a yield of 71% was observed by the analysis of the filtrate using gas chromatography.

Similar reaction to the above by use of dimethylamine, diphenylamine, ammonium acetate, and ammonium carbonate respectively, instead of the triethylamine, gave the desired compound in good yield like the above as shown in Table 3.

TABLE 3

| Solvent | Amine | | Ammonium salt | | Yield (%) |
|---|---|---|---|---|---|
|  | Type | Quantity used (mol ratio) | Type | Quantity used (mol ratio) |  |
| Toluene | Triethylamine | 0.20 | — | — | 71.0 |
| Toluene | — | — | Ammonium acetate | 0.20 | 71.6 |
| Toluene | — | — | Ammonium carbonate | 0.20 | 75.5 |
| Toluene | Diphenylamine | 0.20 | — | — | 70.0 |
| Toluene | Dimethylamine | 0.20 | — | — | 70.3 | in the table, the (mol ratio) of the "quantity used" for amine and ammonium salt means the molar ratio to 2-ethyl-2-propenal.

EXAMPLE 4

Toluene 360 ml, diethyl α-chlorooxalacetate 78.2 g (0.351 mol), and 2-methyl-2-propenal 24.6 g (0.351 mol) were mixed in a glass autoclave. After closing, the temperature in the autoclave was raised to 90° C. Then, with an ammonia pressure held to 1.5 kg/cm² in the autoclave, the inside temperature was raised to 110° C. and the reaction was conducted for 4.5 hours. The contents of the autoclave were cooled to room temperature, and insoluble matters were filtered off. The filtrate was concentrated, and the residue was distilled through Widmer spiral to give 48 g (yield 57.6%) of 5-methyl-2,3-diethoxycarbonylpyridine (bp$_{3.5}$: 160° to 161° C.).

By use of diethyl α-bromooxalacetate instead of diethyl α-chlorooxalacetate, the reaction was carried out in the same manner and gave the desired compound in good yield like the above.

EXAMPLE 5

Diethyl α-chlorooxalacetate 69 g (0.31 mol), 2-ethyl-2-propenal 33 g (0.39 mol), and ammonium acetate 4.8 g (0.06 mol) were mixed in a glass autoclave. After the inside temperature was raised to 110° C., the contents of the autoclave were reacted for 1.5 hours under an ammonia pressure of 0.5 kg/cm², for 1.5 hours under 1.5 kg/cm², AND for 2 hours under 2.5 kg/cm². After completing of the reaction, the reaction mixture was cooled to room temperature. Insoluble matters were filtered off and the filtrate was distilled to give 5-ethyl-2,3-diethoxycarbonylpyridine in a yield of 67%.

EXAMPLE 6

A mixture of diethyl α-chlorooxalacetate 37.6 g (0.168 mol), 2-ethyl-2-butenal 19.6 g (0.20 mol), and chlorobenzene 480 ml were placed in a glass autoclave, and the inside temperature of the autoclave was raised from 35° C. to 105° C. over a period of about 1 hour, while the ammonia pressure being kept to 0.5 kg/cm². After being reacted further 3.5 hours at 105° C., the contents of the autoclave were cooled to room temperature, and insoluble matters were filtered off. The filtrate was concentrated, and the residue was distilled through Widmer spiral to give 6.6 g of 5-ethyl-4-methyl-2,3-diethoxycarbonylpyridine (bp$_2$: 158° to 161° C.).

EXAMPLE 7

In a glass autoclave, diethyl o-bromooxalacetate 25 g (0.094 mol), 2-benzyl-2-propenal 16.4 g (0.112 mol), ammonium acetate 1.5 g, and toluene 200 ml were mixed, and after the inside temperature was raised to 110° C., the mixture was reacted under an ammonia pressure of 0.5 kg/cm² for 12.5 hours. After being cooled to room temperature, the reaction mixture was, with an addition of 40 g of anhydrous sodium sulfate, stirred for one night and solid matters were separated out. The filtrate was concentrated and the residue was distilled to give 8 g of 5-benzyl-2,3-diethoxycarbonylpyridine (bp$_3$: 191° to 194° C.).

IR (Neat): 3000 to 2800, 1700 cm$^{-1}$.

EXAMPLE 8 TO 22

In a similar manner to Example 6, pyridine-2,3-dicarboxylic acid compounds represented by the following formula:

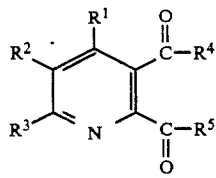

where obtained from adequate starting materials, being hydrolized, as required, in the same manner as shown in Example 1.

TABLE 4

| Example | $R^1$ | $R^2$ | $R^3$ | $R^4$ and $R^5$ | Physical properties |
|---|---|---|---|---|---|
| 8 | H | H | H | $OC_2H_5$ | bp$_3$: 138.5 to 140° C. |
| 9 | H | $CH_3$ | H | $OC_2H_5$ | bp$_{3.5}$: 160 to 161° C. |
| 10 | H | $C_2H_5$ | H | $OC_2H_5$ | bp$_2$: 151 to 152° C. |
| 11 | H | i-$C_3H_7$ | H | $OC_2H_5$ | Oily material |
| 12 | H | n-$C_8H_{17}$ | H | $OC_2H_5$ | Oily material |
| 13 | H | H | $CH_3$ | $OC_2H_5$ | |
| 14 | $CH_3$ | H | H | $OCH_3$ | |
| 15 | n-$C_3H_7$ | $C_2H_5$ | H | $OC_2H_5$ | Oily material |
| 16 | H | H | H | OH | Colorless to light yellow needles |
| 17 | H | $CH_3$ | H | OH | mp: 184 to 186° C. (dec.) |
| 18 | H | $C_2H_5$ | H | OH | mp: 156.5 to 157.5° C. |
| 19 | H | i-$C_3H_7$ | H | OH | |
| 20 | H | H | $CH_3$ | OH | mp: 164 to 166° C. |
| 21 | $CH_3$ | H | H | OH | mp: 190 to 191° C. |
| 22 | H | $C_2H_5$ | $CH_3$ | OH | |

EXAMPLE 23

Glacial acetic acid 100 g and 2-ethyl-2-propenal 30 g (0.357 mol) were placed in a 200 ml four neck distillation flask with a reflux condenser and heated on an oil bath. When the inside temperature reached 90° C., ethyl β-amino-β-ethoxycarbonylacrylate 60 g (0.321 mol) was added dropwise thereto at 90° to 95° C. over a period of 4 hours. After completion of the dropping, the mixture was reacted at 90° to 95° C. for 3 hours. After completion of the reaction, the reaction mixture was distilled to give 36.2 g of 5-ethyl-2,3-diethoxycarbonylpyridine (bp$_2$: 151° to 152° C.).

EXAMPLE 24

In a similar manner to Example 23 by use of propionic acid instead of glacial acetic acid in Example 23, 35.8 g of 5-ethyl-2,3-diethoxycarbonylpyridine was obtained.

EXAMPLE 25

In a similar manner to Example 23 by use of a mixed solvent of glacial acetic acid 30 g and toluene 70 ml instead of glacial acetic acid 100 g in Example 23, 34.8 g of 5-ethyl-2,3-diethoxycarbonylpyridine was obtained.

EXAMPLE 26

In a 500 ml four neck distillation flask with a reflux condenser were placed 2-ethyl-2-propenal 100 g (1.19 mol) and dimethylamine hydrochloride 2.0 g, and heated on an oil bath. When the inside temperature reached 90° C., ethyl β-amino-β-ethoxycarbonylacrylate 200 g (1.07 mol) was added dropwise thereto at 90° to 95° C. over a period of 4 hours. After completion of the dropping, the mixture was heated at 90° to 95° C. for 10 hours. Then, the reaction mixture was cooled to 50° C., and 30 ml of water was added thereto. The mixture was then allowed to stand still to separate into a water layer and an oil layer. The oil layer was distilled to give 123.0 g of 5-ethyl-2,3-diethoxycarbonylpyridine.

EXAMPLE 27

In a similar manner to Example 26 by use of diethylamine hydrochloride instead of dimethylamine hydrochloride in Example 26, 125.0 g of 5-ethyl-2,3-diethoxycarbonylpyridine was obtained.

EXAMPLE 28

Ethyl β-amino-β-ethoxycarbonylacrylate 18.7 g (0.1 mol), 2-methyl-2-propenal 7.5 g (0.107 mol), and glacial acetic acid 50 g were placed in a 100 ml four neck distillation flask with a reflux condenser and the temperature of the mixture was raised to 80° C. on an oil bath over a period of 1 hour. Then, the mixture was reacted at 80° to 85° C. for 5 hours. After completion of the reaction, the reaction mixture was distilled to give 6.8 g of 5-methyl-2,3-diethoxycarbonylpyridine (bp$_{3.5}$: 160° to 161° C.).

EXAMPLE 29 TO 43

By a similar process to Example 28, pyridine-2,3-dicarboxylic acid compounds represented by the following formula:

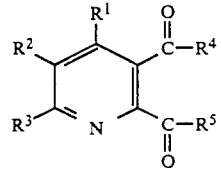

were obtained from adequate starting materials, being hydrolyzed, as required, in the same manner as shown in Example 1.

TABLE 5

| Example | $R^1$ | $R^2$ | $R^3$ | $R^4$ and $R^5$ | Physical properties |
|---|---|---|---|---|---|
| 29 | H | H | H | $OC_2H_5$ | bp$_3$: 138.5 to 140° C. |
| 30 | $CH_3$ | $C_2H_5$ | H | $OC_2H_5$ | bp$_2$: 158 to 161° C. |
| 31 | H | $C_2H_5$ | H | $OC_2H_5$ | bp$_2$: 151 to 152° C. |
| 32 | H | i-$C_3H_7$ | H | $OC_2H_5$ | Oily material |

TABLE 5-continued

| Example | R¹ | R² | R³ | R⁴ and R⁵ | Physical properties |
|---|---|---|---|---|---|
| 33 | H | n-C$_8$H$_{17}$ | H | OC$_2$H$_5$ | Oily material |
| 34 | H | H | CH$_3$ | OC$_2$H$_5$ | |
| 35 | CH$_3$ | H | H | OCH$_3$ | |
| 36 | n-C$_3$H$_7$ | C$_2$H$_5$ | H | OC$_2$H$_5$ | Oily material |
| 37 | H | H | H | OH | Colorless to light yellow needles |
| 38 | H | CH$_3$ | H | OH | mp: 184 to 186° C. (dec.) |
| 39 | H | C$_2$H$_5$ | H | OH | mp: 156.5 to 157.5° C. |
| 40 | H | i-C$_3$H$_7$ | H | OH | |
| 41 | H | H | CH$_3$ | OH | mp: 164 to 166° C. |
| 42 | CH$_3$ | H | H | OH | mp: 190 to 191° C. |
| 43 | H | C$_2$H$_5$ | CH$_3$ | OH | |

EXAMPLE 44

Benzene 225 ml, 90% formic acid 20.5 g (0.401 mol), and ethyl β-amino-β-ethoxycarbonylacrylate 50.0 g (0.267 mol) were placed in a 300 ml four-neck flask equipped with a reflux condenser. After heating the content to 75° C., 2-ethyl-2-propenal 33.7 g (0.401 mol) was added dropwise thereto with air-bubbling and the mixture was reacted at 78°-82° C. for 13 hours. After the reaction, 100 ml of water was added to the mixture and benzene layer was separated from water layer. The benzene layer contained 27.9 g of 5-ethyl-2,3-diethoxycarbonylpyridine (by gas-chromatography).

The above described reaction was carried out using various solvents and acid-catalysts. Table 6 shows solvents, acid-catalysts, reaction conditions and yields of the desired compound.

TABLE 6

| Solvent | Acid catalyst | Reaction temperature (°C.) | Reaction time (hr) | Yield (%) |
|---|---|---|---|---|
| Ethylene glycol | Formic acid | 80 | 7 | 44.1 |
| Sulfolane | Formic acid | 80 | 14 | 45.1 |
| Toluene | Sulfuric acid | 110 | 20 | 38.6 |
| Chlorobenzene | Nitric acid | 90 | 20 | 20.4 |
| Isopropyl alcohol | Formic acid | 80 | 10 | 55.0 |

EXAMPLE 45

Isopropyl alcohol 225 ml and ethyl β-amino-β-ethoxycarbonylacrylate 50.0 g (0.267 mol) were placed in 300 ml four-neck flask equipped with a reflux condenser. After heating the content to 65° C., 33.7 g (0.401 mol) of 2-ethyl-2-propenal and 20.5 (0.401 mol) of 90% formic acid were added dropwise thereto simultaneously with air-bubbling and the mixture was refluxed for 10 hours. After the reaction, isopropyl alcohol was removed from the mixture and the mixture was neutralized with sodium bicarbonate aqueous solution. Oil layer was separated and concentrated under reduced pressure to obtain 71.6 g of oily substance, which was analyzed by gas-chromatography. It was found that the oily substance contained 36.9 g of 5-ethyl-2,3-diethoxycarbonylpyridine.

EXAMPLE 46

Isopropyl alcohol 225 ml, 90% formic acid 20.5 g (0.401 mol) and ethyl β-amino-β-ethoxycarbonylacrylate 50.0 g (0.267 mol) in order were placed in 300 ml four-neck flask equipped with a reflux condenser. After heating the content to 65° C., 2-ethyl-2-propenal 33.7 g (0.401 mol) was added dropwise thereto with air-bubbling and the mixture was refluxed for 10 hours.

After the reaction, isopropyl alcohol was removed from the mixture and the mixture was neutralized with sodium bicarbonate aqueous solution. Oil layer was separated and concentrated under reduced pressure to obtain 71.0 g of oily substance, which was analyzed by gas-chromatography. It was found that the oily substance contained 36.6 g of 5-ethyl-2,3-diethoxycarbonylpyridine.

EXAMPLE 47

Isopropyl alcohol 225 ml and ethyl β-amino-β-ethoxycarbonylacrylate 50.0 g (0.267 mol) were placed in 300 ml four-neck flask equipped with a reflux condenser. After heating the content to 65° C., a mixture of 33.7 g (0.401 mol) of 2-ethyl-2-propenal and 20.5 g (0.401 mol) of 90% formic acid was added dropwise thereto with air-bubbling and the mixture refluxed for 10 hours. The reaction mixture was neutralized with sodium bicarbonate aqueous solution, and separated oil layer was concentrated under reduced pressure to obtain 74.5 g of oily substance, which was analyzed by gaschromatography. It was found that the oily substance contained 36.6 g of 5-ethyl-2,3-diethoxycarbonylpyridine.

EXAMPLE 48

Isopropyl alcohol 225 ml, 90% formic acid 20.5 g (0.401 mol) and ethyl β-amino-β-ethoxycarbonylacrylate 50.0 g (0.267 mol) were placed in 300 ml four-neck flask equipped with a reflux condenser. After heating the content to 65° C., 2-ethyl-2-propenal 33.7 g (0.401 mol) was added dropwise thereto and the mixture was refluxed for 10 hours.

After the reaction, isopropyl alcohol was removed from the mixture and the mixture was neutralized with sodium bicarbonate aqueous solution. Oil layer was separated and concentrated under reduced pressure to obtain 75.5 g of oily substance, which was analyzed by gas-chromatography. It was found that the oily substance contained 33.6 g of 5-ethyl-2,3-diethoxycarbonylpyridine.

EXAMPLE 49

Isopropyl alcohol 150 ml and maleic acid 30.7 g (0 264 mol) were placed in 200 ml four-neck flask equipped with a reflux condenser. After heating the content to 70° C., a mixture of 22.2 g (0.264 mol) of 2-ethyl-2-propenal and 32.9 g (0.176 mol) of ethyl β-amino-β-ethoxycarbonylacrylate were added dropwise thereto with air-bubbling and refluxed for 10 hours. After removal of isopropyl alcohol, 100 ml of water was added thereto and the reaction mixture was neutralized with sodium carbonate. Oil layer was separated and concentrated under reduced pressure to obtain 16.5 g of 5-ethyl-2,3-diethoxycarbonylpyridine.

EXAMPLE 50

In Example 49, maleic acid was replaced by maleic anhydride 12.9 g (0.131 mol) and 22.0 g of 5-ethyl-2,3-diethoxycarbonylpyridine was obtained.

EXAMPLE 51

Isopropyl alcohol 150 ml and sulfamic acid 20.5 (0.211 mol) were placed in 200 ml four-neck flask equipped with a reflux condenser. After heating the content to 70° C., a mixture of 2-ethyl-2-propenal 22.2 g (0.264 mol) and ethyl β-amino-β-ethoxycarbonylacrylate 32.9 g (0.176 mol) was added dropwise thereto with air-bubbling and refluxed for 10 hours. After removing isopropyl alcohol, 130 ml of water was added thereto and the resulting oil layer (57.6 g) was analyzed by gas-chromatography. The oil layer contained 25.0 g of 5-ethyl-2,3-diethoxycarbonylpyridine.

Then, the oil layer was added dropwise to 81 g of 20% sodium hydroxide aqueous solution at 85°-90° C. over a period of 30 minutes and the mixture was refluxed for 30 minutes to hydrolyze. Ethanol thus produced was removed in vacuo. Water 45 g was added thereto, and pH was adjusted to 4 with 63% sulfuric acid at 50°-60° C. and treated with active carbon, which was separated by filtration and the filtrate was treated with 63% sulfuric acid. n-Buthanol 120 ml was added to the mixture and stirred. Butanol layer was separated and concentrated. Crystals thus precipitated were filtered, washed with small amount of ethanol and dried in vacuo to obtain 15 g of 5-ethylpyridine-2,3-dicarboxylic acid.

The above described reaction was repeated varying amount of sulfamic acid used. As is shown in Table 7, 5-ethyl-2,3-diethoxycarbonylpyridine was obtained in good yield.

TABLE 7

| Amount of sulfamic acid used* | Reaction temperature (°C.) | Reaction time (hr) | Yield (%) |
| --- | --- | --- | --- |
| 0.8 | 80 | 10 | 57.3 |
| 0.5 | 80 | 10 | 57.9 |
| 0.1 | 80 | 10 | 56.1 |
| 0.05 | 80 | 10 | 53.1 |

*molar ratio of sulfamic acid to ethyl β-amino-β-ethoxycarbonylacrylate

EXAMPLE 52

Isopropyl alcohol 675 ml and 90% formic acid 61.5 g (1.20 mol) were placed in 1 liter four-neck flask equipped with a reflux condenser. After heating the content to 70° C., 2-methyl-2-propenal 84.3 g (1.20 mol) and ethyl β-amino-β-ethoxycarbonylacrylate 150 g (0.801 mol) were simultaneously added dropwise thereto over a period of 1 hour with air-bubbling and refluxed for 10 hours. After removing isopropyl alcohol, 400 ml of water was added thereto and neutralized with sodium bicarbonate. After standing at 65°-67° C., separated oil layer was concentrated under reduced pressure to obtain 200 g of oily substance, which was distilled under reduced pressure to give 95 g of 5-methyl-2,3-diethoxycarbonylpyridine.

Then, the above described ester 95 g was added dropwise to 330 g of 20% sodium hydroxide aqueous solution at 80°-90° C. over a period of 30 minutes and the mixture was refluxed for 30 minutes to hydrolyze. Ethanol thus produced was removed in vacuo. Water 177 ml was added thereto, and pH was adjusted to 4 with 63% sulfuric acid at 40°-45° C. and treated with active carbon, which was separated by filtration and the filtrate was treated with 63% sulfuric acid. Crystals thus precipitated were filtered, washed with 50 ml of water and dried in vacuo to obtain 62 g of 5-methylpyridine-2,3-dicarboxylic acid.

EXAMPLE 53

Isopropyl alcohol 300 ml and 90% formic acid 12.8 g (0.250 mol) were placed in 500 ml four-neck flask equipped with a reflux condenser. After heating the content to 70° C., a mixture of 2-ethyl-2-butenal 21.6 g (0.22 mol) and ethyl β-amino-β-ethoxycarbonylacrylate 31.1 g (0.166 mol) was added dropwise thereto with air-bubbling and refluxed for 48 hours. To this reaction mixture, conc. hydrochloric acid 10 ml was added dropwise thereto to precipitate remaining ethyl β-amino-β-ethoxy-carbonylacrylate as its hydrochloride form and filtered off at 20° C. Concentration of the filtrate gave 52.2 g of oily substance, which was subjected to silica gel column-chromatography (eluent; ethyl acetate: benzene=1:3) and 10.7 g of 5-ethyl-4-methyl-2,3-diethoxycarbonylpyridine was obtained.

MMR (CDCl$_3$): 1.25 ppm (3H,t), 1.41 ppm (6 H,tx2), 2.35 ppm (3 H,s), 2.74 ppm (2 H,q), 4.45 ppm (4 H,qx2), 8.50 ppm (1 H,s).

What is claimed is:

1. A process for preparing pyridine-2,3-dicarboxylic acid compounds of the formula (1).

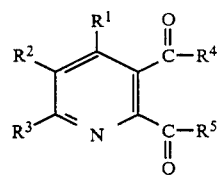
(1)

wherein R$^1$ and R$^3$ are, identical or different, each a hydrogen atom or a lower alkyl group, R$^2$ is a hydrogen atom, a lower alkyl group, or a phenyl-(lower)alkyl group which may have a halogen atom or a lower alkyl group on its phenyl ring, and R$^4$ and R$^5$ are, identical or different, each a lower alkoxy group; comprising reacting a compound of the formula (2):

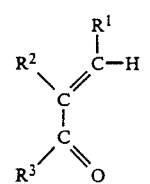
(2)

wherein R$^1$, R$^2$, and R$^3$ are same as defined above, with a compound of the formula (3):

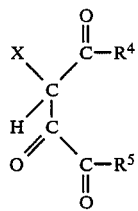

(3)

wherein R⁴ and R⁵ are same as defined above, and X is a halogen atom in the presence of a sufficient amount of ammonia in an aprotic organic solvent under a reaction temperature of from about 20° C. to about 200° C. until the reaction is essentially complete.

2. The process of claim 1, wherein the reaction temperature is from about 70° to 130° C.

3. The process of claim 2, wherein the aprotic organic solvent is immiscible with water.

4. The process of claim 3, wherein the reaction is carried out under pressure.

5. The process of claim 3, wherein the reaction is carried out at atmospheric pressure.

6. The process of claim 4, wherein the reaction is carried out in the presence of a compound selected from the group consisting of a secondary amine, a tertiary amine and an ammonium salt.

7. The process of claim 5, wherein the reaction is carried out in the presence of a compound selected from the group consisting of a secondary amine, a tertiary amine and an ammonium salt.

8. The process of claim 4, wherein $R^1$ and $R^3$ are hydrogen atoms and $R^2$ is a $C_{1-8}$ alkyl group or a phenyl-(lower)alkyl group which may have a halogen atom or a $C_{1-6}$ alky group on its phenyl ring.

9. The process of claim 5, wherein $R^1$ and $R^3$ are hydrogen atoms and $R^2$ is a $C_{1-8}$ akyl group or a phenyl-(lower)alkyl group which may have a halogen atom or a $C_{1-6}$ akyl group on its phenyl ring.

* * * * *

UNITED STATES PATENT AND TRADEMARK OFFICE
CERTIFICATE OF CORRECTION

PATENT NO. : 4,973,695

DATED : November 27, 1990

INVENTOR(S) : Takaharu Yamashita et al.

It is certified that error appears in the above-identified patent and that said Letters Patent is hereby corrected as shown below:

Column 16, line 37;
    Claim 1, line 2, change "(1)." to --(1):--; and
Column 18, line 16;
    Claim 8, line 4, change "alky" to --alkyl--.

Signed and Sealed this

Twenty-first Day of July, 1992

Attest:

DOUGLAS B. COMER

*Attesting Officer*      *Acting Commissioner of Patents and Trademarks*